(12) United States Patent
Charbit et al.

(10) Patent No.: US 6,610,750 B1
(45) Date of Patent: Aug. 26, 2003

(54) TREATMENT OF OSTEOARTHRITIS

(75) Inventors: Suzy Charbit, Creteil (FR); Francois Schutze, St-Nom-La-Breteche (FR); Alain Taccoen, Le Chesnay (FR); Jean-Pierre Pelletier, Saint-Lambert (FR); Diego Provvedini, Bougival (FR)

(73) Assignee: Laboratoires Negma, Magny-les-Hameaux (FR)

( * ) Notice: Subject to any disclaimer, the term of this patent is extended or adjusted under 35 U.S.C. 154(b) by 0 days.

(21) Appl. No.: 09/663,528

(22) Filed: Sep. 15, 2000

(51) Int. Cl.$^7$ ............................................... A61K 31/05
(52) U.S. Cl. ........................................ 514/734; 514/736
(58) Field of Search .................................. 514/734, 736

(56) References Cited

U.S. PATENT DOCUMENTS 4,244,968 A * 1/1981 Friedmann .................... 414/308
5,986,129 A * 11/1999 Di Napoli .................... 562/461

OTHER PUBLICATIONS

Jackson, C.H. et al., Acetaminophen: a practical pharmacologic overview. Can. Med. Assoc. J., 1984, 131: 25–37.

Spangler R.S., Cyclooxygenase 1 and 2 in Rheumatic Disease: Implications for Nonsteroidal Anti–inflammatory Drug Therapy. Arthritis & Rheumatism, 1996, 26: 435–46.

Kalgutkar A.S., Selective cyclooxygenase–2 inhibitors as non–ulcerogenic anti–inflammatory agents, Exp. Opin. Ther. Patents, 1999, 9: 831–49.

Infante R. and Lahita R.G., New disease–modifying and anti–inflammatory drugs. Geriatrics, 2000, 55: 30–40.

Lane N.A., Palm Management in Osteoarthritis: The Role of COX–2 Inhibitors. J. Rheumatol., 1997, 24 (suppl. 49): 20–24.

Hawkey C.J., COX–2 Inhibitors. The Lancet, 1999, 353: 307–14.

American College of Rheumatology., Recommendations for the Medical Management of Osteoarthritis of the Hip and Knee. Arthritis & Rheumatism 2000: 43: 1905–15.

Brandt, K., The Role of Analgesics in the Management of Osteoarthritis Pain. Am. J. Therap., 2000, 7: 75–90.

Wollheim, F., Current Parmacological Treatment of Osteoarthritis, Drugs: 1996, 52 Suppl. 3: 27–38.

Perpoint B. et al., Doing Time Optimizes Sustained–Release Ketoprofen Treatment of Osteoarthritis. Chronobiol. Int., 1994, 11: 119–25.

Le Loet X., Safety of ketoprofen in the Elderly: A Prospective Study on 20,000 Patients. Scand. J. Rheumatol. Suppl., 1989, 83: 21–7.

Jackson L.M. et al., COX–2 Selective Nonsteroidal Anti–Inflammatory Drugs: Do they Really Offer Any Advantages? Drugs, 2000, 69: 1207–16.

Spencer C.M. and Wilde M.I., Diacerin. Drugs, 1997, 53: 98–106.

"Summary of Product Characteristics" (SmPC) of diacerein (the original French version of the SmPC of diacerein, and the English translation.

Dougados M. et al., Evaluation of the Structure–Modifying Effects of Diacerin In Hip Osteoarthritis. Arthritis & Rheumatism 2001, 44: 2539–47.

Fagnani F. et al., Medico–Economic Analysis of Diacerin With or Without Standard Therapy in the Treatment of Osteoarthritis. Pharmacoeconomics, 1998, 13: 135–46.

Dougados M, Nguyen M, Berdah L, Lequesne M, Mazières B, Vignon E 1999; Evaluation of the structural (radiological) effect of diacerein in osteoarthritis of the hip: a 3–year placebo controlled study. Osteoarthritis and Cart 7, Suppl A: 123.

Marcolongo R, Fioravanti A, Adami S, Tozzi E, et al. 1988; Efficacy and tolerability of diacerein in the treatment of osteoarthritis. Curr Ther Res 43: 878–87.

Martel–Pelletier J, Mineau F, Jolicoeur FC, Cloutier JM, Pelletier JP 1998; In vitro effects of diacerein and rhein on interleukin–1 and tumor necrosis factor–alpha systems in human osteoarthritic synovium and chondrocytes. J Rheum 25: 753–62.

Nguyen M, Dougados M, Berdah L, Amor B 1994; Diacerein in the treatment of osteoarthritis of the hip. Arthritis Rheum 37: 529–36.

Pelletier JP, Yaron M, Cohen P 1999; Treatment of osteoarthritis of the knee with diacerein: a double–blind, placebo controlled trial. Arthritis Rheum 42, Suppl. 9: S 295.

Lequesne M, Brandt K. Bellamy N, Moskowitz R, et al. 1994, Guidelines for testing slow acting drugs in osteoarthritis. J Rheum 21, Suppl 41: 65–73.

Ronningen H, Langeland N 1979; Indomethacin treatment in osteoarthritis of the hip joint. Acta Orthop Scand 50: 169–74.

Huskisson EC et al. 1995; Effects of antiinflammatory drugs on the progression of osteoarthritis of the knee. J Rheum 22: 1941–6.

(List continued on next page.)

Primary Examiner—Theodore J. Criares
(74) Attorney, Agent, or Firm—Patterson, Belknap, Webb & Tyler LLP

(57) ABSTRACT

A method of treating osteoarthritis, which is effective not only at targeting the symptoms of the disease, but also in interrupting, preventing, and controlling cartilage destruction, to thereby favorably alter the course of the disease, comprising the administration of an effective amount of rhein or a rhein derivative, preferably diacerein, either alone or in combination with at least one member selected from the group consisting of analgesics, antipyretics, cortico-steroids, anti-inflammatory agents, cyclooxygenase-2 inhibitors, and inflammatory cytokine inhibitors, to a subject in need of such treatment.

18 Claims, No Drawings

OTHER PUBLICATIONS

Rashad S et al. 1989; Effect of non steroidal antiiflammatory drugs on the course of osteoarthritis. Lancet 2: 519–22.

Towheed T, Hochberg M 1997; A systematic review of randomized controlled trials of pharmacological therapy in osteoarthritis of the hip. J Rheum 24: 349–57.

Doherty M. 1989; "Chondroprotection" by non steroidal antiinflammatory drugs. Ann Rheum Dis 48: 619–21.

Pelletier JP, Martel–Pelletier J 1989; The therapeutic effects of NSAID and corticosteroids in osteoarthritis: to be or not to be. J Rheum 16: 266–69.

Vignon E et al. 1990; Cartilage degradative enzymes in human osteoarthritis: effect of a non steroidal antiinflammatory drug administered orally. Semin Arthritis Rheum 19 (suppl 1): 26–9.

Buckland–Wright JC et al. 1995; Quantitative microfocal radiography detects changes in OA knee joint space width in patients in placebo controlled trial of NSAID therapy. J Rheum 22: 937–43.

Brandt K.D., Smith G., Kang S.Y., Myers S., O'connor B., Albrecht M. 1997; Effects of diacerhein in an accelerated canine model of osteoarthritis. Osteoarthritis & Cartilage, 5: 438–49.

McCarthy D 1998: The American Journal of Medicine vol 105 (5A).

Mazières B. 1997: Diacerhein in a post–contusive model of osteoarthritis. Structural results with <<prophylactic>> and <<curative>> regimens. Osteoarthritis & Cartilage, 5 (suppl.A): 7648.

Mazières B., Berdah L. 1993; Effect of diacerheine (ART 50) on an experimental post–contusive model of OA. Osteoarthritis & Cartilage, 1 : 47.

Smith G. N., Myers S. L., Brandt K.D., Mickler E. A., Albrecht M. E. 1999; Diacerhein treatment reduces the severity of osteoarthritis in the canine cruciate–deficiency model of osteoarthritis. Arthritis & Rheumatism, 42: 545–54.

Armstrong CP, Blower AL 1987; Non–steroidal anti–inflammatory drugs and life threatening complications of peptic ulceration. Gut; 28: 527–32.

Bjorkman DJ 1999; Current status of nonsteroidal anti–inflammatory drug (NSAID) use in the United States: risk factors and frequency of complications. Am J Med 107 (6A): 3S–8S.

Drug and Therapeutic bulletin 1987; Which NSAID? DTB 25: 81–4.

Hawkey J 1999; New Drug Classes: COX–2 Inhibitors. Lancet 353: 307–14.

Huskisson EC, et al. 1995; Effects of antiinflammatory drugs on the progression of osteoarthritis of the knee. J Rheumatol 22: 1941–6.

Marcolongo R, Fioravanti A, Adami S, Tozzi E, et al. 1988; Efficacy and tolerability of diacerein in the treatment of osteoarthritis. Curr Ther Res 43: 878–87.

McCarthy D. 1998: Nonsteroidal antiinflammatory drug–related gastrointestinal toxicity: definition and epidemiology. Am J Med; 105 Suppl 3A; 3S–9S.

Towheed TE, Hochberg MC 1997; A systematic review of randomized controlled trials of pharmacological therapy in osteoarthritis of the hip. J Rheumatol 24: 349–57.

Vane JR, Botting RM 1998; Overview: the mechanism of action of anti–inflammatory drugs. In: Clinical significance and potential of selective COX–2 inhibitors. Vane JR and Botting RM, Editors: 1–19. William Harvey Press, London.

Dinarello CA 2000: The role of the Interleukin–1 receptor antagonist in blocking inflammation mediated by Interleukin–1. NEJM 343: 732–4.

Dinarello CA 1991; Interleukin–1 and Interleukin–1 antagonism. Blood 77: 1627–52.

Moore AR, Greenslade KJ, Alam CAS, Willoughby DA 1998; Effects of diacerhein on granuloma–induced cartilage breakdown in the mouse. Osteoarthritis And Cartilage 6: 19–23.

* cited by examiner

TREATMENT OF OSTEOARTHRITIS

The present invention relates to the treatment of rheumatic diseases and more particularly, to the treatment of osteoarthritis by administering an effective amount of rhein or a rhein derivative, most advantageously diacerein.

Heretofore, rheins have been used in human and veterinary therapeutics as the active principles of medicaments, in particular as slow acting anti-inflammatories in the treatment of osteoarthritis. In human treatment, rhein derivatives or diacerein were administered to subjects having active osteoarthritis. The subjects had restricted motion, swelling, and notable pain. Following treatment, in a significant number of instances, the subjects became pain-free, and motion and mobility were restored.

The use of the anti-inflammatory drugs, as well as other analgesic and antipyretic drugs, achieved the goal of controlling pain and functional symptoms of osteoarthritis. This form of treatment addressed the symptoms of the subject, particularly the relief of pain, reduction of swelling, limited mobility, etc.

The causation, initiation and progression of the disease were not addressed in this management program.

The inventors were aware that the initiation and progression of the disease involved progressive degradation of the cartilage matrix.

The objective which the inventors sought to achieve was to interrupt, prevent and control this cartilage destruction and therewith, favorably alter the course of the disease.

This objective was achieved in accordance with the invention by providing a method comprising the administration of an effective amount of rhein or rhein derivatives and, most preferably, diacerein, to subjects demonstrating symptoms of osteoarthritis. The method as already noted is not directed at only treating the symptoms of osteoarthritis, but to interrupting, preventing and controlling cartilage destruction to thereby favorably alter the course of the disease.

Osteoarthritis is a degenerative joint disease characterized by a fragmentation and erosion of the articular cartilage, which becomes soft, frayed and thinned with alteration of the subchondral bone, hypertrophy of the bone, including outgrowths of marginal osteophytes and changes accompanied by pain and stiffness, and finally by loss of function. Osteoarthritis mainly affects the weight bearing joints. When clinically evident, osteoarthritis is a major cause of morbidity and disability, especially for the elderly, due to joint pain, morning stiffness, and limitation of movement and commonly involves the neck, lower back, knees, hips and joints of the fingers. Osteoarthritis can also develop in joints that have suffered injury or trauma in the past, or have been subjected to prolonged heavy use. Osteoarthritis is the most common type of arthritis, occurring in about 10% of the population overall, and affecting approximately 50% of the population over the age of 60. The prevalence of osteoarthritis in women in the age groups under 45 years, 45–60 years and over 65 years is 2%, 30% and 68%, respectively. In men, the prevalence in the same age groups is 3%, 24.5% and 58%, respectively. The prevalence of osteoarthritis will inexorably rise due to the estimated increase of life expectancy. In the developed countries, osteoarthritis is the major cause for hip and knee replacement and, as a cause of invalidism, is surpassed only by the coronary diseases. Osteoarthritis, it can be appreciated, is a major issue for national health.

Although the cause of osteoarthritis is unknown, it is likely that both the initiation and progression of the disease involve mechanical as well as biological events, that result in the progressive degradation of the cartilage matrix associated with variable degrees of osteophytosis, subchondral bone sclerosis and synovial tissue alteration. Osteoarthritis affects all components of the joint, including bone, muscles, tendons, fibrous capsule, synovial membrane and articular cartilage. Cartilage destruction is believed to arise from an imbalance between chondrocyte-controlled anabolic and catabolic processes. Chondrocytes, as well as synoviocytes, maintain cartilage homeostasis, and are activated to increase degradation of the cartilage matrix by inflammatory cytokines, such as Interleukin-1 (IL-1) and tissue necrosis factor-$\alpha$ (TNF-$\alpha$), which are derived from mononuclear cells and macrophages (as well as other cell types), and induce the expression of numerous genes to promote the synthesis of a variety of proteins that contribute to inflammatory events. Accordingly, chondrocytes from osteoarthritis patients have a greater number of IL-1 receptors than cells from healthy individuals.

The main goal for the management of osteoarthritis has been to control pain and functional symptoms of the disease with medical treatment, physiotherapy and patient education.

Osteoarthritis has been treated using anti-inflammatory substances of the cortico-steroid type, e.g., hydrocortisone and betamethasone, which function by virtue of their inhibition of prostaglandin synthesis.

The current pharmacological management of osteoarthritis is based predominantly on the use of classic nonsteroidal anti-inflammatory drugs (NSAIDs) such as ibuprofen and diclofenac, novel NSAIDs such as the inhibitors of cyclooxygenase-2, analgesics such as acetaminophen, and other compounds that belong to distinct classes of drugs, such as diacerein.

Most currently available NSAIDs inhibit both cyclooxygenase 1 (COX-1; constitutive) and cyclooxygenase 2 (COX-2; induced in settings of inflammation) activities, and thereby synthesis of prostaglandins and thromboxane. The inhibition of COX-2 is thought to mediate, at least in part, the antipyretic, analgesic, and anti-inflammatory actions of NSAIDs, but the simultaneous inhibition of COX-1 results in unwanted side effects, particularly those leading to gastric ulcers, that result from decreased prostaglandin formation. NSAIDs include aspirin, which irreversibly acetylates cyclooxygenase, and several other classes of organic acids, including propionic acid derivatives (ibuprofen, naproxen, etc.), acetic acid derivatives (e.g., indomethacin and others), and enolic acids (e.g., piroxicam), all of which compete with arachidonic acid at the active site of cyclooxygenase. Acetaminophen is a very weak anti-inflammatory drug, but is effective as an antipyretic and analgesic agent, and lacks certain side effects of NSAIDs, such as gastrointestinal tract damage and blockade of platelet aggregation.

The following table provides a classification of NSAIDs and other analgesic and antipyretic drugs based on claimed categories.

TABLE 1[1]

Chemical Classification of Analgesic, Antipyretic, and Nonsteroidal Anti-inflammatory Drugs Salicylic acid derivatives Aspirin, sodium salicylate, choline magnesium trisalicylate, salsalate, diflunisal, salicylsalicylic acid, sulfasalazine, olsalazine

TABLE 1[1]-continued

Chemical Classification of Analgesic, Antipyretic, and Nonsteroidal Anti-inflammatory Drugs Para-aminophenol derivatives Acetaminophen
Indole and indene acetic acids Indomethacin, sulindac, etodolac
Heteroaryl acetic acids Tolmetin, diclofenac, ketorolac
Arylpropionic acids Ibuprofen, naproxen, flurbiprofen, ketoprofen, fenoprofen, oxaprozin
Anthranilic acids (fenamates)

Mefenamic acid, meclofenamic acid
Enolic acids

Oxicams (piroxicam, tenoxicam), pyrazolidinediones (phenylbutazone, oxyphenthatrazone)
Alkanones Nabumetone

[1]Goodman and Gilman's The Pharmacological Basis of Therapeutics, 9th Edition, McGraw Hill.

In addition to sharing many therapeutic activities, NSAIDs share several unwanted side effects, outlined in Table 2. The most common is a propensity to induce gastric or intestinal ulceration and bleeding that can be associated with anemia from the resultant blood loss. Patients who use NSAIDs on a chronic basis have about three times greater relative risk for serious adverse gastrointestinal events compared to nonusers. NSAIDs vary considerably in their tendency to cause such erosions and ulcers. Gastric damage by these agents can be brought about by at least two distinct mechanisms. Although local irritation by orally administered drugs allows back diffusion of acid into the gastric mucosa and induces tissue damage, parenteral administration also can cause damage and bleeding, correlated with inhibition of the biosynthesis of prostaglandins, especially $PGI_2$ and $PGE_2$, that serve as cytoprotective agents in the gastric mucosa. These eicosanoids inhibit acid secretion by the stomach, enhance mucosal blood flow, and promote the secretion of cytoprotective mucus in the intestine; inhibition of their synthesis may render the stomach more susceptible to damage. All of the NSAIDs, with the exception of p-aminophenol derivatives, have a tendency to cause gastrointestinal side effects, ranging from mild dyspepsia and heartburn to ulceration of the stomach or duodenum, sometimes with fatal results.

TABLE 2[2]

Side Effects Shared by NSAIDs

Gastrointestinal ulceration and intolerance*
Blockade of platelet aggregation (inhibition of thromboxane synthesis)
Inhibition of uterine motility (prolongation of gestation)
Inhibition of prostaglandin-mediated renal function[†]
Hypersensitivity reactions[‡]

*Lesser side effects with nonacetylated salicylates or p-aminophenol derivatives.
[†]Of special importance for patients with decreased renal blood flow; retention of $NA^+$, $K^+$, and water (edema) can reduce effectiveness of antihypertensive regimens
[‡]Most pronounced with aspirin than with nonacetylated salicylates.
[2]Goodman and Gilman's The Pharmacological Basis of Therapeutics, 9th Edition, McGraw Hill.

Current research has focused on the development of safer NSAIDs, based on a better understanding of their mechanism of action and the pathogenesis of inflammation. The discovery of the existence of at least two isoforms of the enzyme cyclooxygenase (COX) has offered the prospect of devising new, more specific and potentially safer drugs.

Accordingly, a new class of drugs, the inhibitors of cyclooxygenase-2 (COX-2 inhibitors) have been approved, and are under further development, for the treatment of osteoarthritis and other inflammatory diseases. The COX-2 inhibitors (such as celecoxib and rofecoxib) have been shown to be as effective as NSAIDs in the treatment of osteoarthritis with less adverse effects on the upper gastrointestinal tract.

Recent approaches to the treatment of osteoarthritis involve the use of the compound diacerein. This medicinally active compound is known to possess antiarthritic and moderate anti-inflammatory, antipyretic and analgesic activity and has a good safety profile.

Methods have been introduced for the synthesis of diacerein which are simple to carry out and give high yields and in which the diacerein is obtained with a pharmaceutically usable purity with an extremely low residual content of undesired aloe-emodin derivatives or other impurities. It has been established that the latter diacerein compounds, in the form of their pharmaceutical compositions, have favorable therapeutic application in the treatment of inflammatory states such as those of the joints, and in particular, osteoarthritis.

The mechanism of action of diacerein differs from those of NSAIDs or corticosteroids. Diacerein, and more specifically its active diacetyl-derivative rhein, is an IL-1 inhibitor. Indeed, several studies in vitro and with animal models of osteoarthritis have shown that diacerein and rhein inhibit IL-1 and other cytokines (IL-6 and TNF). The above effects explain, at least in part, the beneficial effects of diacerein observed during the symptomatic treatment of osteoarthritis.

Further, neither diacerein nor rhein inhibit prostaglandin biosynthesis; indeed, no inhibitory effect has been detected on the phospholiphase, cyclo-oxygenase or lipo-oxygenase pathways. This unique feature seems to be the reason for the excellent gastric safety profile of diacerein during osteoarthritis treatment.

All of the NSAID compounds (Table 1 above) currently used for the symptomatic treatment of osteoarthritis target only the surface of the disease, namely, the pain and functional impairment.

The ultimate objective is the identification of a novel treatment that not only acts on the symptoms of the disease, and induce a relative short-term benefit for the patient, but also target the underlying pathologies, and therefore may result in a long-term beneficial result. In rheumatology, and in the field of osteoarthritis in particular, the objective has been to identify a drug with a possible "structure-modifying" effect, that is, an effect capable of preventing cartilage degradation. The NSAIDs and analgesics have been tested in animal models for a possible "structure-modifying" effect, with mixed and inconclusive results on cartilage degradation, and no clinically relevant effect in humans in clinical trials. At the present time, no available drug has been demonstrated to have a "structure-modifying" effect, capable of preventing cartilage degradation.

Following the favorable results obtained with diacerein, namely the therapeutic effectiveness with no gastric side effects, the inventors herein investigated whether diacerein might have a possible structure-modifying effect in osteoarthritis patients, and more specifically, the extent, if any, of the effect of treatment with diacerein on cartilage degeneration.

It was surprisingly found that diacerein has a significant effect on cartilage degradation and that the administration of diacerein to patients suffering from this progressive joint disease can be useful, by preventing cartilage degradation.

In order to further explore the potential usefulness of diacerein in the treatment of osteoarthritis, and to closely monitor the relevance of the effects of the treatment by using an accurate radiographic technique, the inventors carried out a 3-year, randomized, double-blind and placebo-controlled multicenter clinical trial in 507 patients with hip osteoarthritis. The unexpected result of the study was that diacerein has a beneficial effect as a structure-modifying treatment for osteoarthritis, as evidenced radiographically by a reduction of the destructive progression of hip osteoarthritis. The results of this study are reported in Dougados M., Nguyen M., Berdah L., Lequesne M., Mazières B., Vignon E. 1999; "Evaluation of the structural (radiological) effect of diacerein in osteoarthritis of the hip: a 3-year placebo controlled study", *Osteoarthritis and Cart* 7, Suppl. A: 123, and are by reference thereto incorporated herein in their entirety.

The foregoing study has been expanded and the results obtained confirm the statistically significant structure-modifying effect of diacerein in osteoarthritis. The ongoing work will be presented by Dougados M., Nguyen M., Berdah L., Mazières B., Vignon E. and Lequesne M. at a meeting of the American College of Rheumatology (ACR) in Philadelphia (Oct. 28–Nov. 2, 2000).

Diacerein (diacetylrhein) of the formula

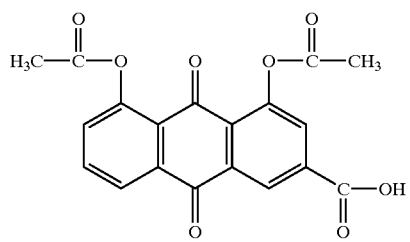

is a medicinally-active compound which possesses anti-arthritic and moderate anti-inflammatory, antipyretic and analgesic activity.

It was not, however, heretofore known that this compound possessed activity for limiting, preventing or interrupting the degradation of cartilage, and, therefore, for treating the course of the disease and not only its symptoms. It is also appreciated, however, that diacerein, in association with NSAIDs and/or analgesics may become an even more particularly valuable compound for the treatment of osteoarthritis.

The different time of onset of the effect of diacerein (≧4 weeks after the start of the treatment) as compared to that of known analgesics, NSAIDs or COX-2 inhibitors, leads to the conclusion that the association of diacerein with an NSAID and/or COX-2 inhibitor may be beneficial for the treatment of osteoarthritis. This conclusion is further supported by evidence that:

diacerein possesses a good gastric safety profile
when the beneficial effect of diacerein are manifested, a reduction in the consumption of analgesics and/or NSAIDs often occurs.

These findings favor the use of the combination of diacerein and NSAID or COX-2 inhibitor or an analgesic for the long-term treatment of osteoarthritis, especially in patients previously treated with drugs potentially harmful to the gastric mucosa. Diacerein can be effectively and safely used in long-term osteoarthritis treatment regimens since:

the effects of diacerein have been shown to persist, even beyond the end of the active treatment period, suggesting that diacerein, unlike NSAIDs, may have an extended "carry-over" effect recently concluded trials yielded the unexpected result that diacerein has positive "disease-modifying" effects on osteoarthritis.

Therefore, the association of diacerein (possessing a slow action on symptoms, and a disease-modifying effect) with an NSAID and/or COX-2 inhibitor (possessing a rapid anti-inflammatory effect, but apparently ineffective or even deleterious on osteoarthritis progression) might have greater potential and wider clinical relevance than the use of either treatment alone.

Diacerein can be prepared by the processes described in U.S. Pat. Nos. 6,057,461 and 5,948,924, and these patents are incorporated herein in their entirety by reference for the purpose of providing preferred methods of producing diacerein.

The diacerein as produced by those processes can be further purified to yield a product of the highest pharmaceutical usable purity using the process described in U.S. Pat. No. 5,756,782, and therefore this patent is incorporated herein in its entirety by reference into this document.

As a general guide to required daily doses, the dosage of diacerein used is between about 25 mg and about 500 mg, and is not dependent on body weight of the patient, at least in adults.

It is not convenient to use diacerein in aqueous solution, because it may not be sufficiently stable in water. Diacerein is virtually insoluble in water and in alcohol, this lack of solubility having to be taken into consideration in its administration.

A particularly preferred pharmaceutical composition for oral administration is described in U.S. Pat. No. 5,952,383. This composition comprises the diacerein, a liquid support oil, a suspension agent, a homogenizing agent, a surfactant, and one or more pharmaceutically acceptable expedients or supports. These compositions are advantageously filled into soft or hard capsules, containing, for example, between 20 mg and 50 mg of active principle per unit.

Another preferred pharmaceutical composition for oral administration is described in U.S. Patent Application MAZAL 09/125,514. This composition is made by comicronization of the rhein or diacerein with sodium lauryl sulfate, the comicronized product in turn being formulated in various conventional application forms.

The entirety of the disclosures of these last two patents are incorporated herein by reference.

Studies have been carried out for establishing the structure-modifying effect of diacerein on joint cartilage, and have confirmed that diacerein is effective in controlling and preventing cartilage destruction in patients with osteoarthritis.

In the studies, the inventors have investigated the structural effect of diacerein, an IL-1 inhibitor, which had previously shown beneficial effects in animal models of osteoarthritis.

In a three-year, randomized, double-blind, placebo-controlled study, 507 patients with severe to moderate hip osteoarthritis were assigned to receive either diacerein, 50 mg twice daily, or an identical placebo. The primary criterion of radiological progression of osteoarthritis was defined by a reduction in the joint space width or at least 0.5 mm during the study. The annual joint space narrowing rate (mm/year) was also determined in the patients who completed the treatment.

A total of 482 patients who had at least two radiographs were evaluated. Baseline characteristics of the 241 patients in each group were similar. In the placebo group, 62.7% of the patients had radiological progression, compared to 53.9% in the diacerein group (log-rank test: p=0.037). Treatment was followed for three years by 269 patients, among whom 55.1% in the placebo group and 41.2% in the diacerein group had radiological progression (log-rank test: p=0.007). Among these 269 patients, the annual joint space narrowing rate was significantly lower in those receiving diacerein than in those receiving placebo (0.18±0.25 versus 0.23±0.23 mm/year respectively; p=0.042).

It was calculated that the diacerein treatment showed a statistically significant structure-modifying effect over the three-year period as compared to placebo.

Because diacerein and rhein inhibit IL-1 and other immune system cytokines, the use of diacerein and rhein are implicated for use in the treatment of inflammatory and autoimmune diseases, including, without limitation, chronic heart failure, psoriatic arthritis, and Wegener's granulomatosis, and other possible related diseases, including, without limitation, endometriosis, bone metastasis, and osteoporosis.

What is claimed is:

1. A method for treating osteoarthritis by delaying the progression of the destruction of joint cartilage comprising the administration of an effective amount of a member selected from a first group consisting of rhein and esters of rhein as the active agent.

2. The method claimed in claim 1 in which the ester of rhein is diacerein.

3. The method claimed in claim 2 in which the effective amount of diacerein is between about 25 mg and about 500 mg per day.

4. The method claimed in claim 2 in which said administration is oral administration.

5. The method claimed in claim 2 in which the effective amount of diacerein is between about 25 mg to about 500 mg, and is in admixture with a pharmaceutically acceptable carrier.

6. The method claimed in claim 2 in which the effective amount of diacerein is between about 50 mg and about 100 mg per day.

7. The method claimed in claim 2 in which the treatment with diacerein is carried out using two daily doses of 50 mg of diacerein.

8. A method of concurrently treating the symptoms of arthritis and delaying the progression of arthritis by controlling the destruction of joint cartilage, comprising administering an effective amount of a member selected from the group consisting of rhein and esters of rhein.

9. The method claimed in claim 8 wherein the ester of rhein is diacerein.

10. The method claimed in claim 9 wherein the effective amount of the diacerein is between about 25 mg and about 500 mg per day.

11. A method of treating osteoarthritis by delaying the progression of the destruction of joint cartilage and relieving symptomatic discomfort, comprising the administration of an effective amount of a member selected from a first group consisting of rhein and esters of rhein; and an effective amount of at least one member selected from a second group consisting of analgesics, antipyretics, corticosteroids, anti-inflammatory agents, cyclooxygenase-2-inhibitors, and cytokine inhibitors.

12. The method claimed in claim 11 wherein the first and second group members are administered together.

13. The method claimed in claim 11 wherein the first and second group members are administered sequentially one after the other.

14. The method of claim 11 wherein the first group member is diacerein and the second group member is a cyclooxygenase-2-inhibitor.

15. The method of claim 1 wherein the need for surgery as a treatment for osteoarthritis is avoided, delayed or reduced by administering the first group member.

16. The method of claim 1, wherein the first group member is administered in association with a treatment to relieve symptomatic discomfort.

17. The method of claim 1 wherein said method of treatment further comprises administering a therapeutically effective amount of at least one member selected from a second group consisting of: (i) an IL-1 synthesis inhibitor, (ii) a TNF-α synthesis inhibitor, (iii) a composition that lowers the levels of IL-1, (iv) a composition that lowers the level of TNF-α, (v) an IL-1 receptor antagonist, (vi) a TNF-α receptor antagonist, (vii) a composition that down-regulates the number of IL-1 receptors, (viii) a composition that down-regulates the number of TNF-α receptors, and (ix) a combination thereof.

18. The method of claim 11 wherein the need for surgery as a treatment for osteoarthritis is avoided, delayed or reduced by administering the first group member.

* * * * *